United States Patent [19]

Cimilluca

[11] Patent Number: 4,512,350

[45] Date of Patent: Apr. 23, 1985

[54] TIME GAIN CONTROL SIGNAL GENERATOR FOR AN ULTRASONIC DIAGNOSTIC SYSTEM

[75] Inventor: Charles I. Cimilluca, Bronx, N.Y.

[73] Assignee: Irex Corporation, Ramsey, N.J.

[21] Appl. No.: 487,788

[22] Filed: Apr. 22, 1983

[51] Int. Cl.³ .............................................. A61B 10/00
[52] U.S. Cl. ...................................... 128/660; 73/631
[58] Field of Search ................................ 128/660–661; 73/631

[56] References Cited

U.S. PATENT DOCUMENTS

| 4,031,743 | 6/1977 | Kossoff et al. | 73/631 X |
| 4,140,107 | 2/1979 | Lancee et al. | 128/660 |
| 4,205,555 | 6/1980 | Hashiguchi | 73/631 X |

Primary Examiner—Kyle L. Howell
Assistant Examiner—Francis J. Jaworski
Attorney, Agent, or Firm—W. Brinton Yorks, Jr.

[57] ABSTRACT

A time gain control signal generator for an ultrasonic diagnostic system is provided which produces a TGC signal which is variable over consecutive, equal duration periods during the reception of ultrasonic echo information. A plurality of controls are set to determine the gains desired during each of the periods. A control signal circuit produces a first signal representative of the time during which the ultrasonic echo information is being received. The first signal energizes the controls. The control signal circuit also produces second signals which apply the gain control signals from the controls to the gain control input of a TGC amplifier during the consecutive periods of the time of ultrasonic information reception.

12 Claims, 6 Drawing Figures

TIME GAIN CONTROL SIGNAL GENERATOR FOR AN ULTRASONIC DIAGNOSTIC SYSTEM

This invention relates to ultrasonic diagnostic systems and, in particular, to a time gain control signal generator for ultrasonic diagnostic systems.

Ultrasonic diagnostic systems operate by transmitting waves of ultrasonic energy into a subject which is being examined. In the case of ultrasonic imaging of the tissue of a patient, the ultrasonic energy passes through the tissue, encountering interfaces between different types of tissue. These tissue interfaces reflect the impinging ultrasonic energy as echoes. A portion of the echo energy travels back to the source of energy, usually an ultrasonic transducer, where the echoes are converted into electrical energy and used to produce an image of the tissue by correlating the times of arrival of various echoes.

Human tissue is not a perfect transmission medium for ultrasound energy, however. As the energy travels through the tissue, it is attenuated, with echoes which travel paths of increasing length generally experiencing greater attenuation. Hence, it is conventional in ultrasound equipment to more strongly amplify echoes received from greater tissue depths. Such controlled amplification is commonly termed time gain control (TGC), since amplifier gain is generally increased following the time of transmission of an ultrasonic wave.

In the case of ultrasonic examination of organs such as the heart, tissues of widely varying ultrasonic transmissive properties are commonly encountered. To compensate for these different transmissive properties it is desirable for the operator to be able to establish a time gain control signal characteristic which is appropriate for the tissue types encountered during a particular procedure. It may be desirable, for instance, to have higher gains for echoes from certain shallow depths, and lower gains for echoes from greater depths during a particular examination.

It is further desirable for the operator to be able to control the depth of tissue being imaged over a considerable range of maximum tissue depths. The depth of tissue being imaged may be controllable over a range of three to one, for example. But regardless of the depth of the image, it is desirable for the operator to have independent incremental control of the time gain control signal for a constant number of tissue depth increments for each image. For example, if the total image depth is seven centimeters and the operator is provided with seven TGC controls, each control should correspond to a different centimeter of tissue depth. And when the image depth is twenty-one centimeters, each of the seven controls should control the gain over a different three centimeter depth of tissue.

In accordance with the principles of the present invention, a time gain control circuit is provided for an ultrasonic diagnostic imaging system. Controls are provided to enable an operator to establish regions of controllable gain over the depth of tissue being imaged. A control signal circuit develops a first signal representative of the depth of tissue being imaged. The first signal is used to energize the controls. The control signal circuit also produces a control signal for each region of controllable gain, which control signal applies gain control signals from the controls to the control input of a TGC amplifier.

Figure 1:
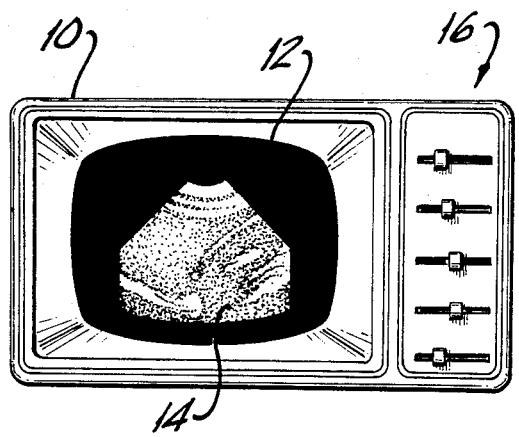
FIG. 1 illustrates the display screen of an ultrasonic diagnostic imaging system with separate regions of TGC control.

Referring to FIG. 1, a display console 10 of an ultrasonic diagnostic imaging system is illustrated. The display console 10 includes a kinescope 12 on which is displayed a sector 14 of tissue being imaged. The skin line of the tissue is located at the top of the sector image 14, with regions of increasing depth shown in the remainder of the sector. To the right of the kinescope 12 are five controls for slide switch potentiometers, indicated generally at 16. The switch controls shown at 16 are aligned generally with regions of increasing depth in the sector image 14. The controls divide the sector image into five regions of controllable gain. The switch control at the top, for instance, will control the gain of the time gain control signal for the first fifth of the image below the skin line, and the bottom switch control will control the gain over the lower fifth of the image. The switch controls 16 are independently adjustable to independently control the gain over five increments of the image 14 in accordance with the specific characteristics of the tissue being imaged.

Figure 2:
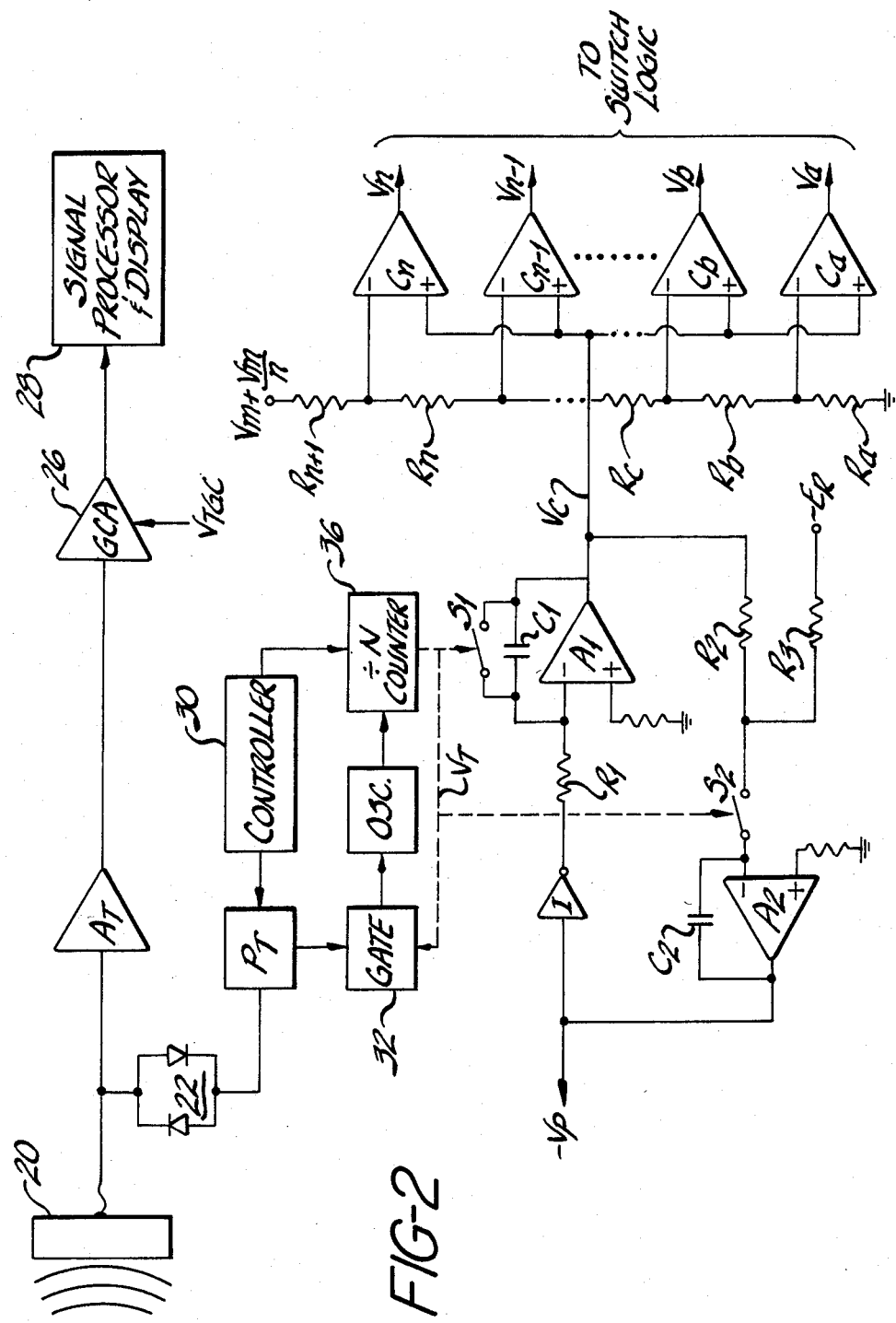
FIG. 2 illustrates an ultrasonic transmission and reception system with a ramp signal generator constructed in accordance with the principles of the present invention for dividing a time interval into equal subintervals.
Figure 3:
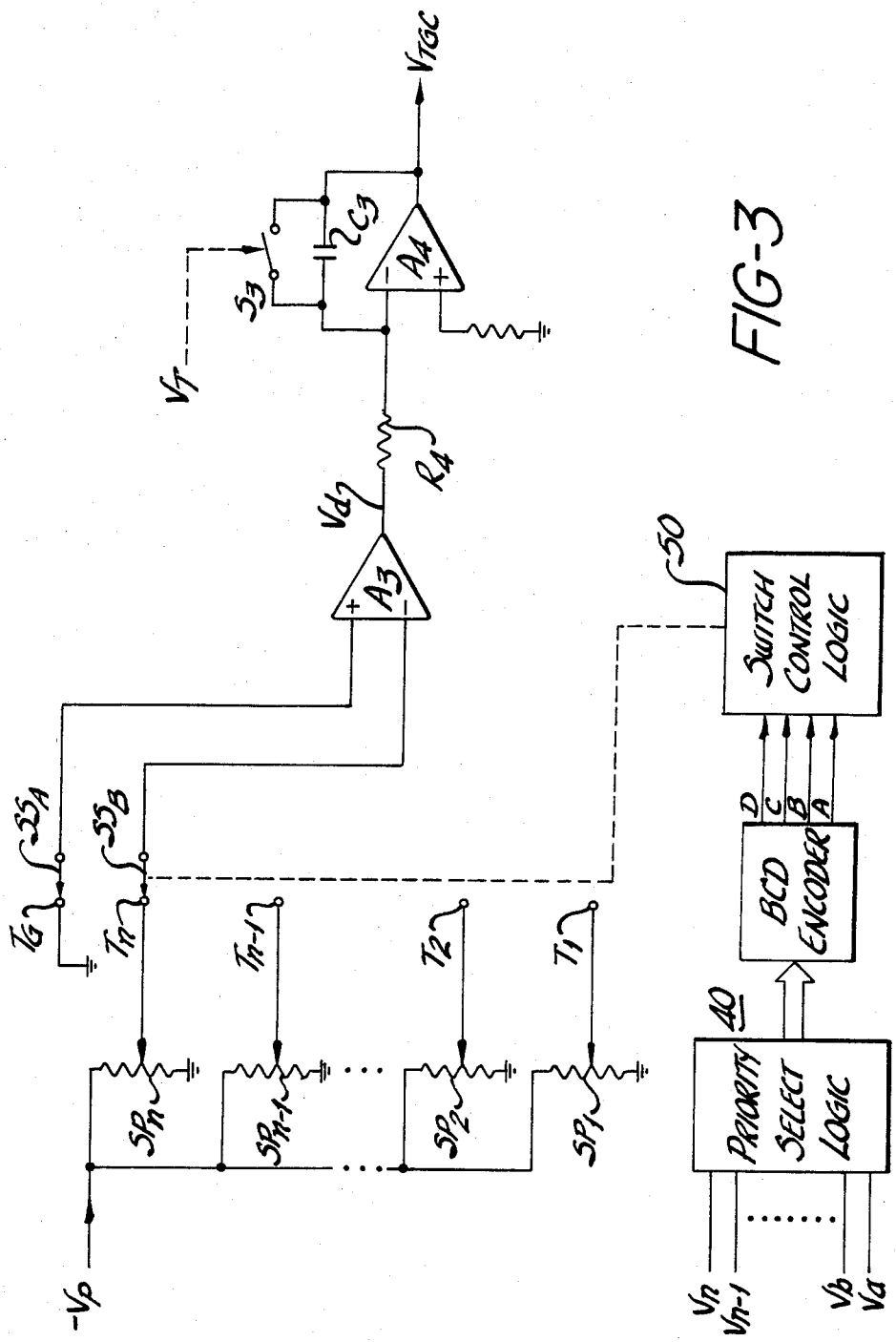
FIG. 3 illustrates a TGC control system operated in conjunction with the ramp signal generator of FIG. 2 to produce a TGC signal in accordance with the principles of the present invention.

A control signal circuit for time gain control signal generation is shown in FIGS. 2 and 3. Referring first to FIG. 2, the transmit/receive circuitry of an ultrasonic diagnostic imaging system is shown partially in block diagram form and partially in schematic diagram form. A controller 30 activates a transducer pulser $P_T$ to initiate the transmission of ultrasonic energy. The pulser $P_T$ produces a high voltage pulse signal, which is coupled by way of parallel reverse connected diodes 22 to a transducer 20. The ultrasonic transducer 20 then transmits waves of ultrasonic energy into the tissue being imaged. Echoes returned by the tissue interfaces are received by the transducer 20, converted into electrical signals and applied to the input of a transducer amplifier $A_T$. The transducer amplifier $A_T$ applies amplified echo signals to the input of a gain control amplifier 26. The gain of the gain control amplifier 26 is controlled by a time gain control signal $V_{TGC}$. The gain controlled echo signals are then applied to signal processor and display apparatus 28 to produce an image such as that shown in FIG. 1.

When the controller 30 activates the $P_T$ pulser, it also loads a number into a divide-by-N counter 36. The divide-by-N counter 36 is now conditioned to count from zero to this number. As the pulser $P_T$ excites the transducer 20, it also sends a signal to a gate 32, which in turn applies a signal to an oscillator, labeled OSC. in FIG. 1, to cause the oscillator OSC. to produce an oscillatory signal. Cycles of the oscillatory signal are counted by the divide-by-N counter 36 until the count reaches the number supplied by the controller. When that number is reached, a $v_T$ signal produced by the divide-by-N counter 36 resets the gate 32 to its initial condition, thereby stopping the oscillator OSC. and the counting process.

The time during which the counter 36 is counting is controllable in accordance with the magnitude of the number supplied by the controller 30. The number supplied by the controller is representative of the depth of the scan 14 of FIG. 1. The time during which the counter 36 is counting is defined as the active interval, which is the period of time required for a wave of ultrasonic energy to travel from the transducer to the most distant portion of the tissue being imaged and for the echoes from that portion of the tissue to return to the transducer and the gain controlled amplifier 36. The active interval is shown as time interval $T_2$ in FIG. 4B. Active interval periods are separated by shorter inactive intervals $T_1$. The high-going signal produced by the counter 36 during the time $T_2$ that it is counting is shown as signal $v_T$ in FIG. 4B. During the active interval time periods $T_2$, the time gain control signal $V_{TGC}$ controls the gain of the gain controlled amplifier 26.

When the $v_T$ signal goes high at the beginning of the active interval, switch $S_1$ is opened, switch $S_2$ closes, and switch $S_3$ in FIG. 3 is opened. The opening and closure of switches $S_1$ and $S_2$ initiate the generation of a ramp signal $v_C$ by the ramp generator loop which includes amplifiers $A_1$ and $A_2$. A feedback capacitor $C_1$ is coupled between the output and the inverting input of amplifier $A_1$. Prior to the start of the active interval switch $S_1$ is closed to discharge capacitor $C_1$ and thus the ramp signal $v_C$ starts from a value of zero. The ramp signal $v_C$ is a time-varying function and takes the form:

$$v_C = \frac{v_P}{R_1 C_1} t \qquad (1)$$

where $C_1$ is the value of capacitor $C_1$, $R_1$ is the value of the input resistor to the inverting input, and $v_P$ is the input voltage to resistor $R_1$. When $v_P$ is a substantially constant voltage, the $v_C$ ramp signal increases linearly with time. The $v_C$ signal is therefore a linear ramp starting at a zero voltage value at the start of the active interval and increasing to $V_m$ at the end of the active interval $T_2$. The average value of the linear ramp waveform during the active interval is thus $V_m/2$.

The $v_C$ ramp signal is supplied to the inverting input of an amplifier $A_2$ by way of a resistor $R_2$, where it is summed with a reference voltage $-E_R$, which is applied by way of a resistor $R_3$. The amplifier $A_2$ includes a feedback capacitor $C_2$, the value of which is chosen together with the values of resistor $R_2$ to provide a time constant which is greater than ten cycles of the ramp signal $v_C$. The output of amplifier $A_2$ may therefore be considered as being constant over the active time interval $T_2$. The output signal of amplifier $A_2$, termed $-v_P$, is applied by way of an inverter I and resistor $R_1$ to amplifier $A_1$.

At the end of the active interval, when the ramp signal $v_C$ is equal to $V_m$, the peak amplitude $V_m$ of the ramp is given by $$V_m = \frac{v_P}{R_1 C_1} T_2 \qquad (2)$$

For practical purposes, the inverting input of amplifier $A_2$ draws substantially no current from the summing junction of resistors $R_2$ and $R_3$. Thus, from summations of the currents conducted by resistors $R_2$ and $R_3$, the following relationships are obtained:

$$\frac{\frac{V_m}{2}}{R_2} = \frac{-E_R}{R_3}, \text{ or } V_m = \frac{-2 R_2 E_R}{R_3} \qquad (3)$$

This expression is seen to be independent to the time $T_2$ and thus the voltage at the output of amplifier $A_2$ is seen to be $$-v_P = \frac{V_m C_1 R_1}{T_2} = \frac{-2(R_2/R_3) E_R C_1 R_1}{T_2} \qquad (4)$$

The ramp signal $v_C$ is applied to a comparator stack including comparators $C_a$, $C_b$, ... $C_{n-1}$, $C_n$. The ramp signal is applied to the positive inputs of the comparators of the stack. The negative inputs of the comparators are coupled to separate tap points of a resistive divider string of equal value resistors, including resistors $R_a$, $R_b$, ... $R_n$, $R_{n+1}$. The voltage applied to the top of the resistor string, $V_m + V_{m/n}$, is divided equally by the resistors. Since the ramp signal $v_C$ is linear with time, and its maximum amplitude $V_m$ is independent of the active time interval, the comparators will switch sequentially from bottom to top to divide the active interval $T_2$ into n equal time intervals. The number of time intervals implemented in a given system is chosen to be equal to the number of control potentiometers on the image display console. The comparators produce output signals $V_a$, $V_b$, ... $V_{n-1}$, $V_n$.

The output signals of the comparator stack of FIG. 2 are applied to the inputs of the priority encoder 40 which is shown in FIG. 3. The switching of the comparator stack signals is sensed by priority select logic, which supplies signals to a binary coded decimal (BCD) encoder. The BCD encoder produces a digital signal indicative of the number of the last comparator signal to switch. For example, if the display console contains seven potentiometer controls, n will equal 7, and the BCD encoder will produce a number over the range of 1-7. The priority encoder 40 is available in integrated circuit form such as the CD40147 type integrated circuit, manufactured by RCA Corporation.

The potentiometers controlled by the slide controls which are shown at 16 in FIG. 1 are shown schematically in FIG. 3 as potentiometers $SP_1$, $SP_2$, ... $SP_{n-1}$, $SP_n$. The arms of the potentiometers are connected to terminals $T_1$ through $T_n$. A further terminal, $T_G$, is connected to ground. Two switches, $SS_A$ and $SS_B$, are controlled to connect any two adjacent terminals to the inputs of a difference amplifier $A_3$. The output of difference amplifier $A_3$ is coupled to the inverting input of an amplifier $A_4$ by a resistor $R_4$. Amplifier $A_4$ is arranged as an integrator with an integrating capacitor $C_3$ to produce the time gain control signal $V_{TGC}$.

Control of the switching of switches $SS_A$ and $SS_B$ is provided by switch control logic 50. The switch control logic 50 is responsive to the BCD encoded number provided by the priority encoder 40 to move the switches $SS_A$ and $SS_B$ down the row of the terminals $T_1$ through $T_G$. For instance, during a first time interval, terminals $T_G$ and $T_n$ are coupled to the inputs of difference amplifier $A_3$ by the switches. During the next time interval, switch $SS_A$ moves down to connect the positive input of different amplifier $A_3$ to terminal $T_n$, and switch $SS_B$ moves down to connect the negative input of difference amplifier $A_3$ to terminal $T_{n-1}$. The switches move progressively down the row of terminals in this manner. The switch control logic 50, the switches $SS_A$ and $SS_B$ and the terminals $T_1$ through $T_G$ may be formed by two analog multiplexer integrated circuits, such as the type CD4051 integrated circuit, manufactured by RCA Corporation. The arms of the potentiometers $SP_1$-$SP_n$ are connected to the analog inputs of the two integrated circuits in sequences which are offset by one from one integrated circuit to the other. The analog outputs of the two multiplexer integrated circuits are connected to the respective inputs of the difference amplifier $A_3$.

Each potentiometer $SP_1$ through $SP_n$ of FIG. 3 produces an independent set point voltage in accordance with the setting of the potentiometer controls. The difference amplifier $A_3$ receives two of these adjacent set point voltages and produces an output voltage which is the difference between the two adjacent set point voltages. This difference voltage is integrated over an interval $t_i$ of the active time interval T in accordance with the function:

$$V_{TGC} = V_s + \frac{V_d/R_4}{C_3} t_i \tag{5}$$

where $V_{TGC}$ is the voltage at the output of amplifier $A_4$ at the end of an interval $t_i$ and $V_s$ is the voltage at the output of ampifier $A_4$ at the start of that incremental interval. This expression is seen to be a linear function of both time and the input voltage to the amplifier $V_d$.

One of the purposes of the present invention is to keep the maximum value of the output voltage $V_{TGC}$ constant independent of the duration of the incremental intervals $t_i$.

This goal is made difficult by the fact that the incremental intervals $t_i$ can vary over a range of three to one in accordance with the variable length of the active time interval $T_2$, and that the $V_{TGC}$ integrator $A_4$ uses fixed value components. Thus, it would ordinarily be expected that the dynamic range of the $V_{TGC}$ control signal would vary as a function of the length of the active interval $T_2$. This expectation does not occur, however, because the set point potentiometers are energized by the $-v_p$ feedback signal of the ramp generator, which is an inverse function of $T_2$.

Since the input voltage $V_d$ to amplifier $A_4$ is a proportion of the voltage $v_p$ applied to each set point potentiometer, $$V_d = Kv_p \tag{6}$$

where K is a constant with a range of zero to one depending upon the setting of the individual potentiometers. Substituting in the equation (4) for $v_p$ shown above, the following expression results:

$$\frac{V_d}{K} = \frac{2(R_2/R_3)E_R\, C_1R_1}{T}, \text{ or } V_d = \frac{2K(R_2/R_3)E_R\, C_1R_1}{T} \tag{7}$$

Substituting the above expression into the expression for $V_{TGC}$ results in:

$$V_{TGC} = V_s + \frac{2K(R_2/R_3)ER\, C_1R_1R_4}{C_3} \left[\frac{t_i}{T}\right] \tag{8}$$

Since the incremental time interval $t_i$ is proportional to the active time interval T by the number of time interval n, $t_i$ can be stated as:

$$t_i = T/n \tag{9}$$

The preceding equation for output signal $V_{TGC}$ then becomes:

$$V_{TGC} = V_s + \frac{2K(R_2/R_3)E_R\, C_1R_1R_4}{C_3} n \tag{10}$$

which is independent of time. It is thus seen that the $V_{TGC}$ signal is a function of the starting voltage of the output signal as determined by the set point voltage value, the integration time constant of output amplifier $A_4$, and the values of the components in the ramp generator feedback loop. In practical application, the values of the integrator including input resistor $R_4$ and integrating capacitor $C_3$ are chosen to allow the amplifier to integrate over the full dynamic range of the $V_{TGC}$ voltage in one incremental time period $t_i$ of minimal duration.

Operating of the TGC signal generator of the present invention may alternatively be viewed in a different way. From preceding equation (3) it was seen that the ramp signal $V_c$ always attains the same final value $V_m$, regardless of the length of the active interval (the duration of the ramp). Since the ramp always starts from zero, it follows that the ramp must have a steep slope during a short active interval, and a relatively gradual slope during a relatively longer active interval if it is always to attain the same final value.

In the ramp generator circuit of FIG. 2, it is seen that the ramp signal $v_c$ is obtained by integrating the $v_p$ signal. Mathematically the $v_p$ signal must functionally represent the slope of the ramp, since it is the slope of a line which is integrated to produce the line. The equation (4) supports this analysis, which shows that the magnitude of the $v_p$ signal is inversely related to the magnitude of the active interval $T_2$. The greater (longer) the active interval $T_2$, the smaller the magnitude of $v_p$, which corresponds to the more gradual slopes of ramps of increasing duration. Thus the $v_p$ signal varies in relation to the slope of the ramp for any active interval duration.

The present inventor has recognized that the desired TGC signal must vary from one set point value to the next during each time increment of the active interval. Since the TGC signal $V_{TGC}$ is developed by integration of the $V_d$ signal, the $V_d$ signal must be representative of the slope of the TGC signal between each pair of set point values. This is the case, since adjacent set point values are subtracted by amplifier $A_3$ to produce an amplitude change between set points. But the time during which the amplitude change must occur is variable as a function of the duration of the active time interval $T_2$: the shorter the active time interval, the more quickly must the transition from one set point value to the next occur. Hence, the shorter the active time interval, the greater the slope of each increment of the TGC signal. The present inventor has discovered that the necessary variation of the slope of each time increment of the TGC signal is provided by deriving the set point voltages from the ramp-slope representative $v_p$ signal. The $V_{TGC}$ signal will thereby occupy a constant dynamic range regardless of the variation of set point values and active interval durations.

Figure 4A:
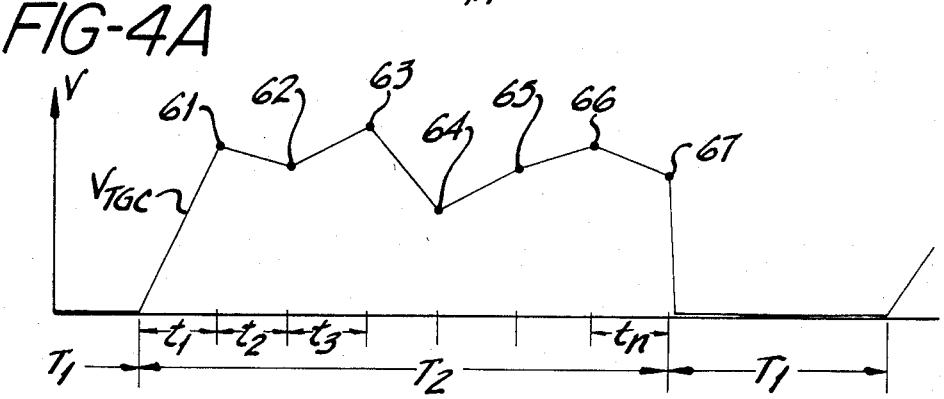
FIGS. 4A, 4B and 4C illustrate waveforms used to explain the operation of the arrangement of FIGS. 2 and 3.
Figure 4B:
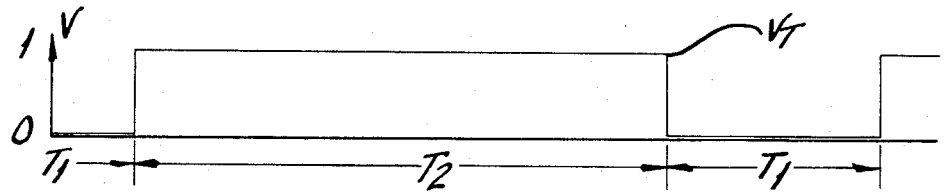
Figure 4C:
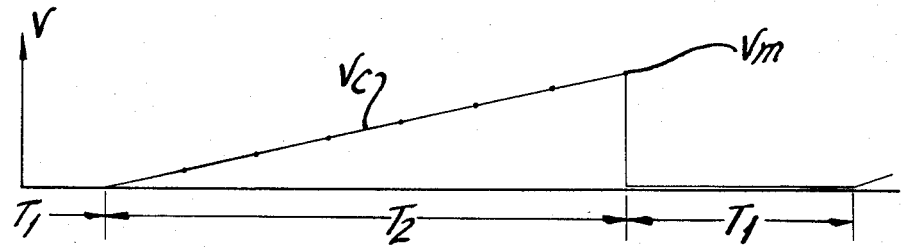

Signals illustrating the operation of the circuitry of FIGS. 2 and 3 are shown in FIGS. 4A, 4B, and 4C. The active time interval, $T_2$, is representively shown in FIG. 4B. The linear ramp generator signal $v_C$ is representatively shown in FIG. 4C, and is seen to attain a maximum value $V_m$ at the end of the active time interval $T_2$. The dotted points shown along the ramping $v_C$ signal represent the equal time intervals into which the signal is divided by the comparator stack. The comparator stack divides the active time interval into incremental inervals $t_1, t_2, t_3, \ldots t_n$, as shown at the baseline of FIG. 4A. Seven set point voltages 61–67 are representively shown in FIG. 4A. The time gain control voltage $V_{TGC}$ is shown in FIG. 4A, which is the result of integration in accordance with the voltage differential between adjacent set point values as modified by the slope ($v_p$) of the ramp signal during the active interval.

What is claimed is:

1. In an ultrasonic diagnostic imaging system which transmits ultrasound into the tissue of a patient and is capable of receiving ultrasonic echo information from varying tissue depths during active intervals, a time gain control circuit for controllably amplifying received ultrasonic echo information during consecutive reception periods of said active intervals comprising:

a gain controlled amplifier having an input responsive to received ultrasonic echo information signals, an output at which amplified echo information signals are produced, and a control input responsive to a time gain control signal;

means, operated in response to the transmission of ultrasound, for producing a first signal representative of the durations of said active intervals and a second signal representative of the durations of said consecutive periods;

gain set means for selecting the gain of said amplifier during respective ones of said consecutive periods, said gain set means being responsive to said first signal for producing a plurality of gain control signals; and means, responsive to said second signal, for applying said gain control signals to said control input of said gain controlled amplifier during said consecutive periods.

2. The arrangement of claim 1, wherein said first and second signal producing means comprises a ramp signal generator circuit for producing a ramp signal during each of said active intervals, and said first signal comprises a ramp slope signal which is inversely proportional to the durations of said active intervals.

3. The arrangement of claim 2, wherein said first and second signal producing means further comprises comparison means responsive to said ramp signal for producing said second signal.

4. The arrangement of claim 3, wherein said gain control signal applying means comprises:

controlled switch means, responsive to said second signal, for applying pairs of said gain control signals to inputs of a difference amplifier;

a difference ampler having inputs coupled to said controlled switch means and an output for producing a difference signal; and an integrator having an input coupled to the output of said difference amplifier and an output coupled to the control input of said gain controlled amplifier.

5. In an ultrasonic diagnostic imaging system which transmits ultrasound into the tissue of a patient and is capable of receiving ultrasonic echo information from varying tissue depths, a time gain control circuit for controllably amplifying received ultrasonic echo information during consecutive reception periods of relatively equal time duration comprising:

a gain controlled amplifier having an input responsive to received ultrasonic echo information signals, an output at which amplified echo information signals are produced, and a control input responsive to a time gain control signal;

a ramp signal generator circuit which is activated during active time intervals when ultrasonic echo information signals are received by said amplifier, for producing a ramp signal having a slope which is inversely proportional to the duration of said active time intervals and a slope signal representative of said ramp signal slope;

a plurality of gain setting means for setting the desired gain of said amplifier during each of a plurality of consecutive periods of said active time intervals, said gain setting means being energized by said slope signal for producing a plurality of consecutive gain signals;

means, responsive to said ramp signal, for producing sequential difference signals which represent the difference between pairs of said gain signals produced by said gain setting means during said consecutive periods; and means for applying said sequential difference signals to said control input of said gain controlled amplifier.

6. The arrangement of claim 5, wherein said ramp signal generator circuit includes a feedback signal path for producing said slope signal, wherein said ramp signal has a duration which is substantially equal to the duration of an active time interval, and an amplitude at the end of said interval which is substantially constant regardless of the duration of said interval.

7. The arrangement of claim 6, wherein each of said gain setting means comprises a potentiometer.

8. The arrangement of claim 7, wherein said sequential difference signal producing means comprises:

comparison means, responsive to said ramp signal, for producing equal period signals corresponding to said consecutive periods;

a difference amplifier having first and second inputs and an output; and controlled switch means, responsive to said equal period signals, for applying two of said consecutive gain signals to said inputs of said difference amplifier during each of said consecutive, relatively equal periods.

9. The arrangement of claim 8, wherein said sequential difference signal applying means comprises an integrator having an input coupled to the output of said difference amplifier and an output coupled to the control input of said gain controlled amplifier.

10. The arrangement of claim 8, wherein said comparison means comprises a tapped voltage divider and a plurality of comparators, each comparator having a first input coupled to receive said ramp signal and a second input coupled to a respective tap of said voltage divider.

11. The arrangement of claim 5, wherein said ramp signal generator circuit includes first and second integrators coupled in a feedback loop, said first integrator exhibits a relatively short time constant for producing said ramp signal, and said second integrator exhibits a relatively long time constant relative to that of said first integrator and said active time intervals for producing said slope signal.

12. The arrangement of claim 11, wherein the output of said first integrator is coupled to the input of said second integrator and the output of said second integrator is coupled to the input of said first integrator, wherein said feedback loop is opened between ones of said active time intervals.

* * * * *